(12) United States Patent
Du Preez (10) Patent No.: US 7,888,390 B2
(45) Date of Patent: *Feb. 15, 2011

(54) PREPARATION OF PLATINUM(II) COMPLEXES

(75) Inventor: Jan Gysbert Hermanus Du Preez, Port Elizabeth (ZA)

(73) Assignee: Platco Technologies (Proprietary) Limited, Port Elizabeth (ZA)

( * ) Notice: Subject to any disclaimer, the term of this patent is extended or adjusted under 35 U.S.C. 154(b) by 0 days.

This patent is subject to a terminal disclaimer.

(21) Appl. No.: 12/491,148

(22) Filed: Jun. 24, 2009

(65) Prior Publication Data

US 2009/0312417 A1 Dec. 17, 2009

Related U.S. Application Data

(63) Continuation of application No. 10/580,425, filed as application No. PCT/IB2004/003855 on Nov. 24, 2004, now Pat. No. 7,576,126.

(60) Provisional application No. 60/524,727, filed on Nov. 25, 2003.

(51) Int. Cl.
A61K 31/28 (2006.01)
C07F 15/00 (2006.01)

(52) U.S. Cl. ........................... 514/492; 556/137
(58) Field of Classification Search ............... 556/137; 514/492
See application file for complete search history.

(56) References Cited

U.S. PATENT DOCUMENTS

| | | | |
|---|---|---|---|
| 4,169,846 | A | 10/1979 | Kidani et al. |
| 4,536,571 | A | 8/1985 | Stockel et al. |
| 5,281,447 | A | 1/1994 | Brady et al. |
| 5,290,961 | A | 3/1994 | Okamoto et al. |
| 5,338,874 | A | 8/1994 | Nakanishi et al. |
| 5,420,319 | A | 5/1995 | Okamoto et al. |
| 5,716,988 | A | 2/1998 | Ibrahim et al. |
| 5,959,133 | A | 9/1999 | Ohnishi |
| 6,376,057 | B1 | 4/2002 | Akao et al. |
| 6,866,857 | B1 | 3/2005 | Mauvernay |
| 7,070,796 | B1 | 7/2006 | Ibrahim et al. |
| 7,122,668 | B2 | 10/2006 | Barenholz et al. |
| 7,208,616 | B2 | 4/2007 | Menez et al. |
| 7,309,796 | B2 | 12/2007 | Pepels et al. |
| 7,351,846 | B2 | 4/2008 | Zák et al. |
| 7,576,126 | B2 * | 8/2009 | Du Preez ............ 514/492 |
| 2004/0186172 | A1 | 9/2004 | Ibrahim |
| 2006/0063833 | A1 | 3/2006 | Schridde et al. |
| 2006/0275331 | A1 | 12/2006 | Zaludek et al. |
| 2007/0073074 | A1 | 3/2007 | Zak et al. |
| 2007/0167643 | A1 | 7/2007 | Du Preez |
| 2007/0197811 | A1 | 8/2007 | Menez et al. |
| 2008/0064895 | A1 | 3/2008 | Du Perez |
| 2009/0312417 | A1 | 12/2009 | Du Preez |

FOREIGN PATENT DOCUMENTS

| | | |
|---|---|---|
| EP | 0 115 929 A0 | 8/1984 |
| EP | 0 345 356 A1 | 12/1989 |
| EP | 0 345 356 A4 | 12/1989 |
| EP | 0 567 438 B1 | 10/1993 |
| EP | 0 617 043 B1 | 9/1994 |
| EP | 0 625 523 B1 | 11/1994 |
| EP | 0 715 854 B1 | 6/1996 |
| EP | 0 774 963 B1 | 5/1997 |
| EP | 0 801 070 B1 | 10/1997 |
| EP | 0 881 226 B1 | 12/1998 |
| EP | 0 943 331 B1 | 9/1999 |
| EP | 1 121 117 B1 | 8/2001 |
| EP | 1 207 875 B1 | 5/2002 |
| EP | 1 308 453 A2 | 5/2003 |
| EP | 1 308 453 A3 | 5/2003 |
| EP | 1 308 454 B1 | 5/2003 |
| EP | 1 561 754 B1 | 8/2005 |
| EP | 1 680 434 B1 | 7/2006 |
| EP | 1 704 156 A0 | 9/2006 |

(Continued)

OTHER PUBLICATIONS

Bierbach, U. et al. (1998, e-pub. Jan. 31, 1998). "Modification of Platinum(II) Antitumor Complexes with Sulfur Ligands. 1. Synthesis, Structure, and Spectroscopic Properties of Cationic Complexes of the Types [PtCl(diamine)(L)]$NO_3$ and [{PtCl(diamine)}$_2$(L-L)]$(NO_3)_2$ (L=Monofunctional Thiourea Derivative; L-L=Bifunctional Thiourea Derivative)," *Inorg. Chem.* 37(4):708-716.

(Continued)

*Primary Examiner*—Porfirio Nazario Gonzalez
(74) *Attorney, Agent, or Firm*—Morrison & Foerster LLP (57) ABSTRACT

The invention relates to a method for the preparation of platinum (II) complexes, in particular dicarboxylatoplatinum (II) complexes containing a neutral bidentate ligand, such as oxaliplatin. The method includes the step of reacting a bis-dicarboxylatoplatinate (II) species with a suitable neutral bidentate ligand to form a neutral dicarboxylatoplatinum (II) complex and, if necessary, recrystallizing the product to form a pure dicarboxylatoplatinum (II) complex containing a neutral bidentate ligand. The invention also relates to a method for producing a bis-dicarboxylatoplatinate (II) species, and to new platinum (II) complexes that can be made by the method of the invention.

10 Claims, 5 Drawing Sheets

FOREIGN PATENT DOCUMENTS

| | | | |
|---|---|---|---|
| GB | 2 210 039 | A | 6/1989 |
| JP | 5-301884 | A | 11/1993 |
| WO | WO-03/004505 | A1 | 1/2003 |
| WO | WO-2005/051966 | A1 | 6/2005 |
| WO | WO-2005/075489 | A1 | 8/2005 |
| WO | WO-2006/023154 | A1 | 3/2006 |
| WO | WO-2006/024897 | A1 | 3/2006 |
| WO | WO-2006/108428 | A1 | 10/2006 |
| WO | WO-2007/085957 | A1 | 8/2007 |

OTHER PUBLICATIONS

Database CA [Online] Chemical Abstracts Service, Columbus, Ohio, US; Abel, Edward W. et al: "Platinum metal complexes of potentially chelating alkene thioether and selenoether ligands: the synthesis and dynamic nuclear magnetic resonance study of [MX2{E[(CH2)nCR:CR2]2}] (M=Pt or Pd; X=Cl, Br, or I; E=S or Se; n=2 or 3; R=H or Me) and the x-ray crystal structure of cis-diiodo(5-thi" retrieved from STN Database accession No. 1990:235576, Journal of the Chemical Society, Dalton Transactions: Inorganic Chemistry (1972-1999) (11):2315-2321, CODEN: JCDTBI; ISSN: 0300-9246, 1989 (Abstract only).

Database CA [Online] Chemical Abstracts Service, Columbus, Ohio, US; Abel, Edward W. et al: "Platinum metal complexes of potentially chelating alkene-thioether and alkene-selenoether ligands: synthesis and dynamic nuclear magnetic resonance study of [MX2{MeE(CH2)nCH=CH2}] (M=platinum or palladium; X=Cl, Br, or I; E=S or Se; n=2 or 3) and the x-ray structure of cis-dibromo(2-thia-6-heptene)platinum(II)," retrieved from STN Database accession No. 1990:56232, Journal of the Chemical Society, Dalton Transactions: Inorganic Chemistry (1972-1999) 11:2315-2321, CODEN: JCDTBI; ISSN: 0300-9246, 1989 (Abstract only).

Database CA [Online] Chemical Abstracts Service, Columbus, Ohio, US; Abel, Edward W. et al: "Synthetic, dynamic nuclear magnetic resonance and crystallographic studies of platinum complexes containing silyl-substituted dialkenyl-thioether and—selenoether ligands," retrieved from STN Database accession No. 1995:114833, abstract, compound I & Journal of the Chemical Society, Dalton Transactions: Inorgamic Chemistry (1972-1999) 18:2637-2643, CODEN: JCDTBI; ISSN: 0300-9246, 1994 (Abstract only).

Database CA [Online] Chemical Abstracts Service, Columbus, Ohio, US; Balakrishna, Maravanji S. et al: "Heterodifunctional ligands derived from monooxidized bis(phosphino)amines. Synthesis and transition metal (molybdenum(O), tungsten(O), rhodium(I), palladium(II), and platinum(II)) complexes of (diphenylphosphino)(diphenylphosphinothio lyl)- and (diphenylphosphino)(disphenylphosphinoselen oyl)phenylam," retrieved from STN Database accession No. 1993:685076, abstract & Inorganic Chemistry 32(25):5676-5681, CODEN: INOCAJ; ISSN: 0020-1669, 1993 (Abstract only).

Database CA [Online] Chemical Abstracts Service, Columbus, Ohio, US; Belletti, Daniele et al: "Reactivity of Ph2(2-C5H4N)Pse towards Ru3(CO)12 and mononuclear MCl2(PhCN)2 (M=Pd or Pt) complexes," retrieved from STN Database accession No. 2003:483190, Inorganica Chimica Acta 350:421-427, CODEN: ICHAA3; ISSN: 0020-1693, 2003 (Abstract only).

Database CA [Online] Chemical Abstracts Service, Columbus, Ohio, US; Bhasin, Kuldip K. et al: "2,5-Diselena-3,3,4,4-tetrafluorohexane and 2,5-diselena-1,1,1,6,6,6- hexafluorohexane and their platinum and palladium chloride complexes," retrieved from STN Database accession No. 1979:567640, Journal of Fluorine Chemistry 14(2):171-176, CODEN: JFLCAR; ISSN: 0022-1139, 1979 (Abstract only).

Database CA [Online] Chemical Abstracts Service, Columbus, Ohio, US; Clarke, M. L. et al: "First examples of M-Se-P-N-N heterocycles," retrieved from STN Database accession No. 2001:237332, Inorganic Chemistry Communications 4(3):115-118, CODEN: ICCOFP; ISSN:1387-7003, 2001 (Abstract only).

Database CA [Online] Chemical Abstracts Service, Columbus, Ohio, US; Harbron, Stephen K. et al: "Coordination chemistry of higher oxidation states. Part 24. Palladium(IV) and nickel(III) complexes of hybrid thio- and seleno-ether ligands," retrieved from STN Database accession No. 1987:589472, Inorganica Chimica Acta 130(1):43-47, CODEN: ICHAA3; ISSN: 0020-1693, 1987 (Abstract only).

Database CA [Online] Chemical Abstracts Service, Columbus, Ohio, US; Kemmitt, Tim et al: "Chelating ditelluroether complexes of palladium and platinum: synthesis and multinuclear NMR studies. Structure of dibromo(meso-1,3-bis(phenyltelluro)propane )palladium(II): [Pd{meso-PhTe(CH2)3TePh}Br2]," retrieved from STN Database accession No. 1989:87401, Inorganic Chemistry 28(4):692-696, CODEN: INOCAJ; ISSN: 0020-1669, 1989 (Abstract only).

Database CA [Online] Chemical Abstracts Service, Columbus, Ohio, US; Khanna, Anju et al: "Synthesis and multinuclear NMR studies of 3-aminopropyl(aryl)chalcogenides, NH2CH2CH2CH2Ear (E=Se, Te), and their complexes with Pt(II) and Pd(II)," retrieved from STN Database accession No. 1995:569289. Journal of Organometallic Chemistry 494(1-2):199-204, CODEN: JORCAI; ISSN:0022-328X, 1995 (Abstract only).

Database CA [Online] Chemical Abstracts Service, Columbus, Ohio, US; Khuzaie, Rula F. et al: Screening for anticomplementary activity of some platinum (II) and palladium (II) complexes with various donor ligands and anions, XP002317068 retrieved from STN Database accession No. 2002:445382, Oriental Journal of Chemistry 18(1):1-6, CODEN: OJCHEG; ISSN: 0970- 020X, 2002 (Abstract only).

Database CA [Online] Chemical Abstracts Service, Columbus, Ohio, US; Knorr, Michael et al: "Synthesis and molecular structures of platinum and mercury complexes chelated by (phenylthiomethyl)silane ligands," retrieved from STN Database accession No. 2004:973319, Zeitschrift Fuer Anorganische und Allegemeine Chemie 630(12):1955-1961, CODEN: ZAACAB; ISSN: 0044-2313, Oct. 21, 2004 (Abstract only).

Database CA [Online] Chemical Abstracts Service, Columbus, Ohio, US; Mizuno, Masagi: "Linear chain compound bisoxalatoplatinate complexes," XP002317074 retrieved from STN Database accession No. 1989:432596, Kagaku Kogyo Shiryo (Tsukuba, Japan) 23(5):201-216, CODEN: KKSHEP; ISSN: 0288-8882, 1989 (Abstract only).

Database CA [Online] Chemical Abstracts Service, Columbus, Ohio, US; Prignano, Andrea L. et al: "Silica-anchored bis(trialkylphosphine) platinum oxalate: a photogenerated catalyst for olefin hydrosilation," XP002317070 retrieved from STN Database accession No. 1987:77537, Monatshefte Fuer Chemie 117(5):617-619, CODEN: MOCMB7; ISSN: 0026-9247, 1986 (Abstract only).

Database CA [Online] Chemical Abstracts Service, Columbus, Ohio, US; Puniyani, Sushil et al: "Platinum (II) complexes of cyclohexanone and cyclopentanone thiosemicarbazones," XP002317071 retrieved from STN Database accession No. 1985:447222 Indian Journal of Chemistry, Section A: Inorganic, Physical, Theoretical & Analytical 24a(3):240-241, CODEN: IJCADU; ISSN: 0376-4710, 1985 (Abstract only).

Database CA [Online] Chemical Abstracts Service, Columbus, Ohio, US; Rashan, Luay J. et al: "In vitro antitumor activity of platinum (II) complexes with various nitrogen containing ligands," XP002317069 retrieved from STN Database accession No. 1998:522331, Biologica (Bratislava) 53(3):349-352, CODEN: BLOAAO; ISSN: 0006-3088, 1998 (Abstract only).

Database CA [Online] Chemical Abstracts Service, Columbus, Ohio, US; Song, Rita et al: "Synthesis and selective tumor targeting properties of water soluble porphyrin-Pt(II) conjugates," [Erratum to document cited is CA137:362598] XP002317067 retrieved from STN Database accession No. 2002:85473, Journal of Inorganic Biochemistry 92(3-4):200, CODEN: JIBIDJ; ISSN: 0162-0134, 2002. Erratum found in Database CA [Online] Chemical Abstracts Service, Columbus, Ohio, US; Song, Rita et al: "Synthesis and selective tumor targeting properties of water soluble porphyrin-Pt(II) conjugates," retrieved from STN Database accession No. 2002:249587 Journal of Inorganic Biochemistry 89(1-2):83-88, CODEN: JIBIDJ; ISSN: 0162-0134, 2002 (Abstract only).

Database CA [Online] Chemical Abstracts Service, Columbus, Ohio, US; Syamal, A. et al: "Synthesis of new platinum (II) complexes with ethanethiolamine, o-aminothiophenol and bidentate carboxylic acids," XP002317072 retrieved from STN Database accession No. 1983: 209058, Revue de Chimie Minerale 20(1):123-128, CODEN: RVCMA8; ISSN: 0035-1032, 1983 (Abstract only).

Database CA [Online] Chemical Abstracts Service, Columbus, Ohio, US; Uttecht, J.-G. et al: "Synthesis, vibrational spectra and normal coordinate analysis of (n-Bu4N)2 [Pt(SCN)n(ox)], n=2, 4, and crystal structure of [(C5H5N)2CH2][Pt(SCN)4(ox)]," XP002317073 retrieved from STN Database accession No. 2002:781520, Zeitschrift Fuer Naturforschung, B: Chemical Sciences 57(9):1036-1042, CODEN: ZNBSEN; ISSN: 0932-0776, 2002 (Abstract only).

Gladiali, S. et al. (1988). "Synthesis, Structure, and Dynamic Behaviour of Transition Metal Chelate Complexes with Atropismeric Dithioether Ligands" *Eur. J. Inorg. Chem.* pp. 113-118.

Gümüs, F. et al. (2003). "Synthesis, Characterization and In Vitro Cytotoxic, Mutagenic and Antimicrobial Activity of Platinum(II) Complexes with Substituted Benzimidazole Ligands," *J. Inorg. Biochem.* 94(3):255-262.

International Preliminary Report on Patentability mailed on Nov. 23, 2005, for PCT Patent Application No. PCT/IB2004/003855, filed on Nov. 24, 2003, 20 pages.

International Preliminary Report on Patentability mailed on Mar. 1, 2007, for PCT Patent Application No. PCT/IB2005/000570, filed on Mar. 7, 2005, 28 pages.

International Preliminary Report on Patentability mailed on Aug. 5, 2008, for PCT Patent Application No. PCT/IB2007/000213, filed on Jan. 30, 2007, 6 pages.

International Search Report mailed on Mar. 23, 2005 for PCT Patent Application No. PCT/IB2004/003855, filed on Nov. 24, 2004, 5 pages.

International Search Report mailed on Aug. 2, 2005, for PCT Patent Application No. PCT/IB2005/000570, filed on Mar. 7, 2005, 7 pages.

International Search Report mailed on Jun. 11, 2007, for PCT Patent Application No. PCT/IB2007/000213, filed on Jan. 30, 2007, 2 pages.

Khokhar, A.R. et al. (1985). "The Synthesis and Antitumor Properties of a Series of Water Soluble Carboxylato-(1,2-diaminocyclohexane) Platinum(II) Complexes", *Inorganica Chimica Acta* 108:63-66.

Mizuno, M. (1988). "Linear Chain Compound Bisoxalatoplatinate Complexes," *Kagaku Kogyo Shiryo* 23(5):201-216. (Japanese language only.) [See English abstract citation above: Database CA [Online] . . . STN Database accession No. 1989:432596.].

Pasini, A., et al. (1989). "A New Synthetic Method for Diaminomalonatoplatinum Type Complexes and the Unexpected Behavior of [PtCl$_2$(trans-dach)]," *Inorganic Chemical* 152, Italy (1988), pp. 19-20.

Puniyani, S. et al. Platinum(II) Complexes of Cyclohexanone and Cyclopentanone Thiosemicarbazones, *India Journal of Chemistry, Section A: Inorganic, Physical, Theoretical & Analytical* 24A(3):240-241.

Reedijk, J. (1999, e-pub. Aug. 21, 1999). "Why Does Cisplatin Reach Guanine-N7 with Competing S-Donor Ligands Available in the Cell?" *Chem. Rev.* 99(9):2499-2510.

Schanz, H.-J. et al. (2003). "Improved Resolution Methods for (R,R)- and (S,S)- cyclohexane-1,2-diamine and (R)- and (S)-BINOL", *Tetrahedron: Asymmetry* 14(18):2763-2769.

Shriver, D.F., ed. (1979). "Partially Oxidized Potassium Bis(oxalate)palatinate," *Inorganic Syntheses*, vol. 19, John Wiley and Sons: New York, NY, one page.

Thornber, C.W. (1979). "Isosterism and Molecular Modification in Drug Design," *Chemical Society Reviews* [Chemical Society, London, GB] 8(4):563-580.

Written Opinion mailed on mailed on Mar. 21, 2006, for PCT Patent Application No. PCT/IB2004/003855, filed on Nov. 24, 2004, 12 pages.

Written Opinion mailed on Mar. 1, 2007, for PCT Patent Application No. PCT/IB2005/000570, filed on Mar. 7, 2005, 10 pages.

Written Opinion mailed on Aug. 5, 2008, for PCT Patent Application No. PCT/IB2007/000213, filed on Jan. 30, 2007, 5 pages.

U.S. Appl. No. 12/162,745, filed Jan. 30, 2007, for De Preez.

Syamal, A et al. (Dec. 20, 1982). "Platinum (II and IV) Complexes with NS and No Donor Ligands," *Current Science* 51(24):1153-1155.

\* cited by examiner

PREPARATION OF PLATINUM(II) COMPLEXES

CROSS-REFERENCE TO RELATED APPLICATIONS

This application is a continuation of U.S. patent application Ser. No. 10/580,425, having a 371 filing date of Feb. 9, 2007, which is a National Phase filing under 35 U.S.C. §371 of International Application No. PCT/IB2004/003855, filed on Nov. 24, 2004, which claims priority to U.S. Provisional Patent Application No. 60/524,727, filed on Nov. 25, 2003. The contents of these applications are incorporated herein by reference in their entireties.

BACKGROUND OF THE INVENTION

THIS invention relates to the preparation of platinum(II) complexes, in particular the preparation of dicarboxylatoplatinum(II) complexes containing a neutral bidentate ligand, (such as oxaliplatin, which has become increasingly important due to its anti-cancer activity).

Dicarboxylatoplatinum(II) complexes (such as oxaliplatin) containing a neutral bidentate ligand ("non-leaving group") have in the past been synthesized by way of a process that utilizes a silver salt to remove halide ions from the complex. The use of a silver compound in the process results in numerous contaminants, which must be removed by further processes in order to achieve purity that is suitable for anti-cancer pharmaceutical agent purposes.

Oxaliplatin and its pharmaceutical properties were first disclosed by Kidani et al. in J Med Chem, 1978, 21, 13135 and in U.S. Pat. No. 4,169,846. In this patent a halogenoplatinum compound is used as the starting material. Halide ions are removed by a silver salt, whereafter an oxalate is introduced either as the free acid or a salt thereof.

In general, a method for the production of oxaliplatin is as set out below:

Step 1.

$X=Cl, Br, I$ and L=trans-1-1,2-diaminocyclohexane

Step 2.

or $Y=SO_4^{2-}$

Step 3.

$Z=K^+$, $Na^+$ or $H^+$

U.S. Pat. No. 5,290,961 in the name of Tanaka Kikinzoku Kogyo K.K. teaches that the abovementioned method has the disadvantage that many impurities are incorporated into the products. These impurities include unreacted $PtLX_2$, AgX and $Ag^+$. The presence of $PtLX_2$ is attributed to their generally insoluble nature in water. As a result, large quantities of water must be used in step 2 to dissolve $PtLX_2$. This prevents the AgX, even though it is insoluble in water, from being completely removed from the solution. U.S. Pat. Nos. 5,338,874 and 5,420,319, also in the name of Tanaka Kikinzoku Kogyo K.K., teach processes for the production of cis-oxalato(trans-l-1,2-cyclohexanediamine)platinum(II) with high optical purity which can be used as an active pharmaceutical ingredient of a carcinostatic agent. However, these processes also follow complicated multi-step pathways, making use of silver compounds which must also ultimately be removed from the process.

SUMMARY OF THE INVENTION

The present invention has been made to address the drawbacks of the prior art, in terms of which dicarboxylatoplatinum(II) complexes containing a neutral bidentate ligand, such as oxaliplatin, are produced using the silver method, which results in contaminants in the final product, is time consuming and expensive. Furthermore, the absence of silver compounds in the process enables the synthesis of a group of novel platinum compounds i.e. ligands containing donor atoms other than N such as S or Se.

A first aspect of the invention relates to a method for the preparation of a platinum(II) complex, in particular a dicarboxylatoplatinum(II) complex containing a neutral bidentate ligand, such as oxaliplatin, the method including the step of reacting a bis-dicarboxylatoplatinate(II) species with a suitable neutral bidentate ligand to form a neutral dicarboxylatoplatinum(II) complex and if necessary recrystallising the product to form a pure dicarboxylatoplatinum(II) complex containing a neutral bidentate ligand.

The bis-oxalatoplatinate(II) species and ligand are typically reacted at a temperature of 40° C. to 100° C., preferably approximately 95° C., for a period of 0.5 to 3 hours, preferably 1 hour.

Any dicarboxylatoplatinate(II) species may be removed from the product by dissolving the product in distilled water and adding an oxalate such as $Cs_2C_2O_4$, which transforms the dicarboxylatoplatinate(II) species into a species that can be separated from the dissolved product by filtration.

The neutral bidentate ligand is typically an amine.

The amine may be a diamine.

Where the method is for the preparation of chemically and optically pure oxaliplatin, the ligand is optically pure trans-1-1,2-diaminocyclohexane.

The neutral bidentate ligand may contain donor atoms other than N, or N together with a donor atom other than N, typically S and Se, for example:

neutral bidentate heterocyclic amines with an S donor atom (for example thioethereal groups), such as:

1-alkyl/aryl-2-alkylthioalkyl/aryl heterocyclic amines, particularly imidazoles or pyridines, for example:
Ligand (i) 1-methyl-2-methylthioethylimidazole
Ligand (ii) 1-methyl-2-methylthiopropylimidazole
Ligand (iii) 1-butyl-2-methylthiomethylimidazole
Ligand (iv) 1-methyl-2-methylthiomethylimidazole
Ligand (v) 1-butyl-2-methylthioethylimidazole
Ligand (vi) 2-methylthiomethylpyridine
Ligand (vii) 2-methylthioethylpyridine
Ligand (viii) 2-methylthiopropylpyridine;
aminoalkylthioalkyl/aryl compounds for example:
Ligand (ix) 1-amino-2-thiomethylethane
Ligand (x) 1-amino-2-thioethylethane;
dithioethers for example:
Ligand (xi) 2,5-dithiahexane;
diseleno ethers for example:
Ligand (xii) 2,5-diseleno hexane; etc.

New oxalatoplatinum(II) complexes containing S or Se donor atoms that can be prepared using the method of the invention include:

Complex (i) oxalato(1-methyl-2-methylthioethylimidazole)platinum(II)
Complex (ii) oxalato(1-methyl-2-methylthiopropylimidazole)platinum(II)
Complex (iii) oxalato(1-butyl-2-methylthiomethylimidazole)platinum(II)
Complex (iv) oxalato(1-methyl-2-methylthiomethylimidazole)platinum(II)
Complex (v) oxalato(1-butyl-2-methylthioethylimidazole)platinum(II)
Complex (vi) oxalato(2-methylthiomethylpyridine)platinum(II)
Complex (vii) oxalato(1-amino-2-thioethylpyridine)platinum(II)
Complex (viii) oxalato(1-amino-2-thiopropylpyridine)platinum(II)
Complex (ix) oxalato(1-amino-2-thiomethylethane)platinum(II)
Complex (x) oxalato(1-amino-2-thioethylethane)platinum(II)
Complex (xi) oxalato(2,5-dithiahexane)platinum(II)
Complex (xii) oxalato(2,5-diseleno hexane)platinum(II).

The above new complexes may be used in methods of treating cancer in patients, and in methods of manufacturing medicaments for treating cancer in patients The complexes produced according to the method of the invention contain no traces of silver.

A second aspect of this invention is a method for producing a bis-dicarboxylatoplatinate(II) species, e.g. a bis-oxalatoplatinate(II) salt which may be used in the method of the first aspect of the invention. The method according to the second aspect of the invention includes the step of either reacting a platinum(II) compound, such as $K_2PtX_4$ or reacting a platinum(IV) compound such as $K_2PtX_6$ where X is a halide such Cl, Br or I, preferably Cl, with a dicarboxylate such as an oxalate, wherein the platinum(II) or platinum(IV) compound and oxalate salt are reacted at a high mole ratio of greater than 1:4, preferably 1:8 or greater, more preferably 1:16 or greater most preferably 1:24 or greater.

In the case of the platinum(IV) compound, this compound is reduced to platinum(II) by the oxalate, or it may be reduced by another reducing agent such as $SO_2$ or sulfite.

The oxalate is typically $K_2C_2O_4$.

The platinum(II) bis-dicarboxylato species is typically $K_2Pt(C_2O_4)_2.2H_2O$.

The platinum(II) compound or platinum(IV) compound and oxalate are typically reacted at a temperature of from 40° C. to less than 100° C., preferably approximately 95° C., for a period of 0.5 to 4 hours, typically 1 hour.

DESCRIPTION OF PREFERRED EMBODIMENTS

This invention relates to a method for the preparation of platinum(II) complexes, in particular a dicarboxylatoplatinum(II) complex containing a neutral bidentate ligand ("non-leaving group") such as oxaliplatin, and new platinum(II) complexes that include a donor atom other than N, the method includes the steps of:

Step 1. the production of a bis-dicarboxylatoplatinate(II) species, typically $K_2Pt(C_2O_4)_2.2H_2O$;

Step 2. reaction of the bis-dicarboxylatoplatinate(II) species with a suitable neutral bidentate ligand to form a dicarboxalatoplatinum(II) complex containing a neutral bidentate ligand product; and if necessary Step 3. recrystallising the product to form a pure oxalatoplatinum(II) complex containing a neutral bidentate ligand product.

Step 1

The reaction times quoted in all of these steps are given for reagent quantities of ~10 g.

A bis-dicarboxylatoplatinate(II) species such as $K_2Pt(C_2O_4)_2.2H_2O$ may be synthesized using either $K_2PtCl_6$, or $K_2PtCl_4$ as starting materials. It may be possible to use $H_2PtCl_6$ as a starting material.

Method 1—Synthesis of $K_2Pt(C_2O_4)_2.2H_2O$ Using $K_2PtCl_4$ $K_2PtCl_4$ and $K_2C_2O_4$ may be dissolved in distilled water in the mole ratio of 1:16 and stirred at a temperature of between 40° C. to 100° C., typically approximately 95° C. for 0.5 to 2 hours, typically 1 hour. The solution is refrigerated at a temperature from 2° C. to 10° C., typically approximately 5° C. for 0.5 to 2 hours typically 1 hour to complete crystallization where after it may be filtered. The precipitated product may be washed 5 times with small volumes of cold water and once with acetone and allowed to air dry.

1 mol $K_2PtCl_4$+16 mol $K_2C_2O_4 \rightarrow K_2Pt(C_2O_4)_2.2H_2O$

Method 2—Synthesis of $K_2Pt(C_2O_4)_2.2H_2O$ Using $K_2PtCl_6$ (Oxalate Acting as Reducing and Complexing Agent)

Figure 2:
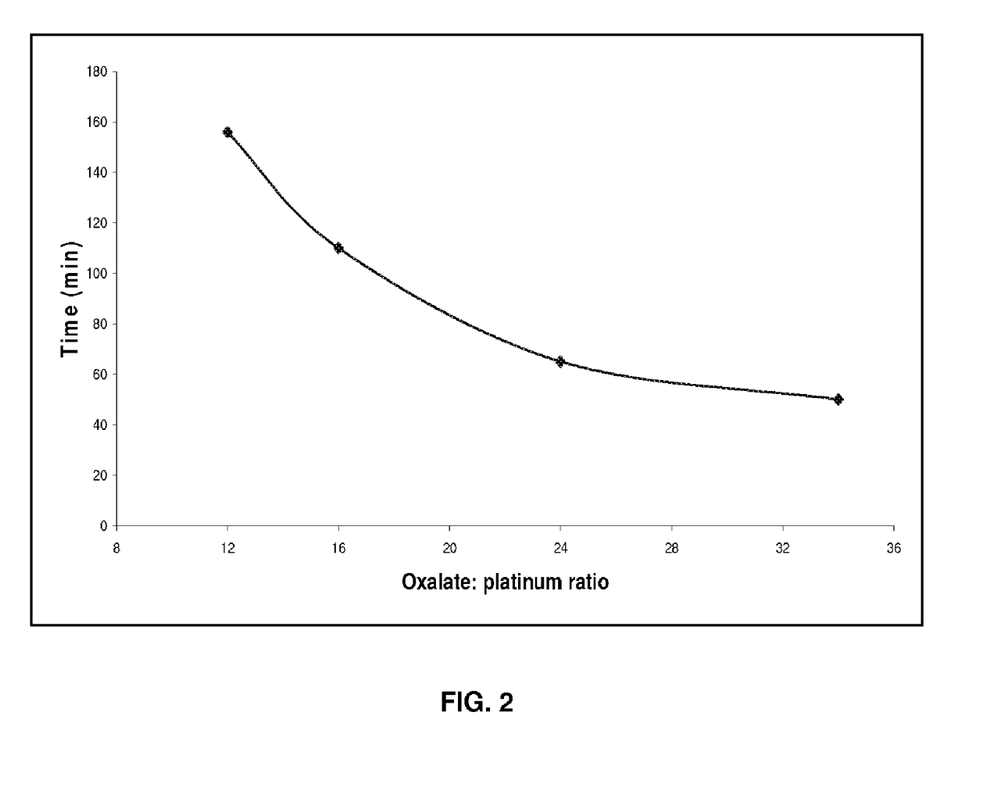
FIG. 2 is a graph indicating the time taken to reach an 85% yield of $K_2Pt(C_2O_4)_2.2H_2O$ relative to the oxalate to platinum ratio in the reaction of $K_2C_2O_4$ with $K_2PtCl_6$ at 95° C.

$K_2C_2O_4$ and $K_2PtCl_6$ may be suspended in water in a mole ratio of 34:1 and stirred at a temperature of between 40° C. to 100° C., typically approximately 95° C. for 0.5 to 4 hours typically 55 minutes as illustrated by the curve in FIG. 2. Only 10 minutes additional time is required for a ratio of 24:1. The reaction vessel may be maintained at a temperature between 2° C. to 10° C., typically approximately 5° C. for 0.5 to 2 hours typically 1 hour to allow for complete crystallization followed by filtration. The precipitate may be washed 5 times with small volumes of cold water and once with acetone and allowed to air dry.

1 mol $K_2PtCl_6$+34 mol $K_2C_2O_4 \rightarrow K_2Pt(C_2O_4)_2.2H_2O$

In this reaction the oxalate plays two roles. Firstly, it acts as a reducing agent. On heating the solution of $K_2C_2O_4$ with a suspension of $K_2PtCl_6$ the latter dissolves to form a dark orange solution with the evolution of gas. The disappearance of the starting material accompanied with a darkening of the solution indicates the formation of $PtCl_4^{2-}$ therefore a reduction of platinum(IV) to platinum(II). The evolution of gas further indicates the oxidation of oxalate to $CO_2$.

After all the $K_2PtCl_6$ has dissolved, the oxalate starts a second role where it acts as a complexing agent and a light yellow precipitate starts to form. Thus the oxalate acts as a suitable complexing agent which can coordinate to the platinum to form $K_2Pt(C_2O_4)_2.2H_2O$. Therefore, this method can be divided into two separate reactions. An alternative reducing agent such as $SO_2$ may be used in the place of the oxalate, to reduce the platinum IV to platinum II.

In prior art methods which describe the synthesis of $K_2Pt(C_2O_4)_2.2H_2O$, a small excess of $K_2C_2O_4$ of up to 4 times was used at a temperature of 100° C. for an extensive period (up to 18 hrs). See Shriver D F (Ed) 1979. Inorganic Synthesis, Vol. XIX: 16-17. During that time reduction of the platinum species occurs forming platinum metal (platinum black).

Figure 1:
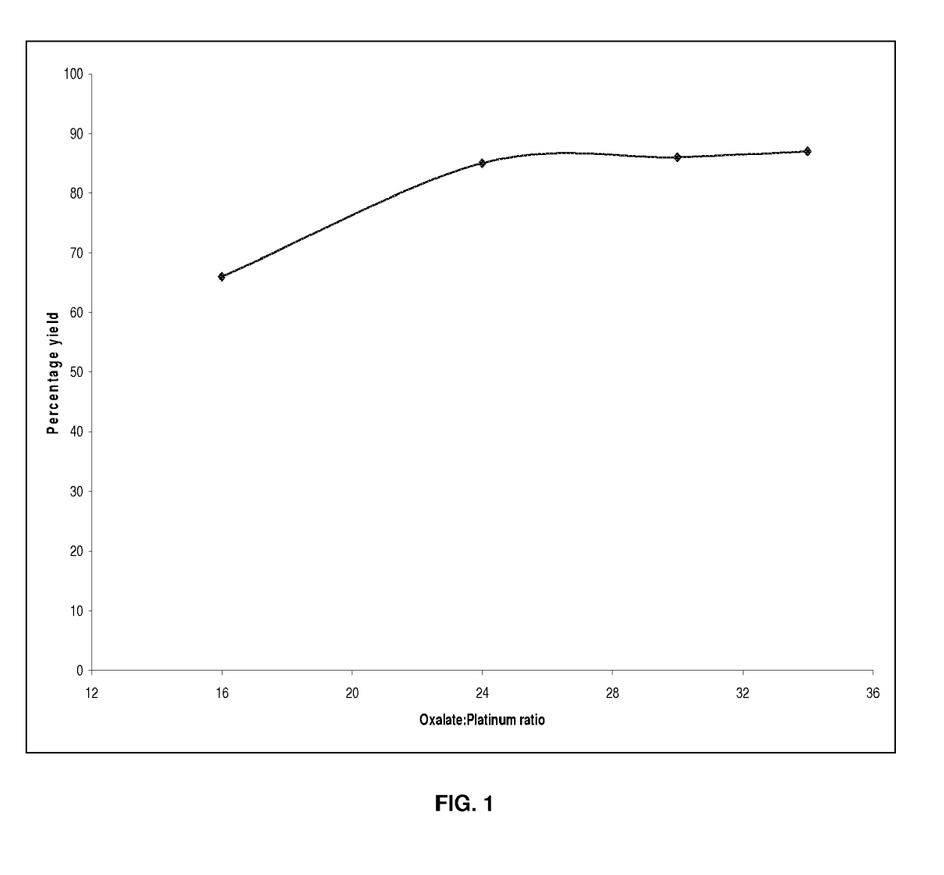
FIG. 1 is a graph indicating the efficiency of the synthesis of $K_2Pt(C_2O_4)_2.2H_2O$ relative to the ratio of $K_2C_2O_4$ to $K_2PtCl_6$ in a reaction of $K_2PtCl_6$ with $K_2C_2O_4$ with a constant reaction time of 1 h 15 min at 95° C.

In accordance with an aspect of the method of this invention, the inventor has quite unexpectedly found out that when a platinum compound and oxalate are reacted at a high mole ratio of greater than 1:4, preferably greater than 1:8, more preferably greater than 1:16, most preferably 1:24 or greater and lower reaction temperatures (less than 100° C., typically 95° C.), shorter reaction times are attained and no reduction to platinum metal (no platinum black) is observed. The higher concentration of the complexing anion, oxalate, not only acts as a stabilizater of the bis-oxalatoplatinate(II) species but also improves reaction rates as well as ligand exchange thus resulting in high yields of the bis-oxalatoplatinate(II) species. The larger the excess oxalate used, the higher the percentage yield of $K_2Pt(C_2O_4)_2.2H_2O$. (See FIG. 1), when a 1:16 ratio of $K_2C_2O_4$ is used relative to $K_2PtCl_6$, the yield of $K_2Pt(C_2O_4)_2.2H_2O$ is only 67%. The yield consistently increases as the oxalate excess increases such that a ratio of 34:1 results in a 86% yield (See FIG. 2). In FIG. 2 the ratio of platinum to potassium oxalate is plotted against the time in minutes required to reach the maximum yield of the production of $K_2Pt(C_2O_4)_2.2H_2O$ from $K_2PtCl_6$, namely ~85%. Experiments performed with ratios of 8:1 or lower resulted in the formation of finely divided black platinum metal due to decomposition. This gradually occurs upon heating for approximately 8½ hours. When ratios of 3:1-8:1 are employed, extensive reaction time periods are required to reach maximum efficiencies of conversions, which still results in low yields. In the literature, a ratio of 3:1 results in a 30% yield after refluxing for 18 hours (1080 mins) (Synthesis of $K_2Pt(C_2O_4)_2.2H_2O$, Shriver, D. F., Inorganic Synthesis, 19, pp. 16-17, (ed.). 1979). As the amount of oxalate increases, the time taken to reach the 85% yield decreases from 156 mins at a mole ratio 12:1, to 110 mins at a mole ratio of 16:1, to 65 mins at a mole ration of 24:1 to 55 mins at a mole ratio of 34:1.

Step 2

The bis-dicarboxylatoplatinate(II) species viz. $K_2Pt(C_2O_4)_2.2H_2O$, may be reacted with a suitable, preferably optically pure, neutral bidentate ligand to form a neutral platinum(II) oxalato compound such as oxaliplatin.

$K_2Pt(C_2O_4)_2.2H_2O$ may be dissolved in a suitable solvent system whereafter a ligand (L) dissolved in a suitable solvent is added. The ligand may be selected from any bidentate neutral donor ligand, but in the case of oxaliplatin is a diamine, namely optically pure trans-l-1-1,2-diaminocyclohexane. Optically pure trans-l-1-1,2-diaminocyclohexane may be obtained in an optically pure state by crystallization with tartaric acid, for example by a method described by Hans-Jörg Schanz, Michael A. Linseis and Declan G. Gilheany, in Improved resolution methods for (R,R)- and (S,S)-cyclohexane-1,2-diamine and (R)- and (S)-Binol. Tetrahedron Asymmetry 12 (2003), 2763-2769, the content of which is incorporated herein by reference. The solution may be maintained at a temperature from 40 to 100° C., typically approximately 95° C. for 0.5 to 2 hours, typically 1 hour to form a precipitate which contains oxalatoplatinum(II) complex such as oxaliplatin.

1 mol $K_2Pt(C_2O_4)_2.2H_2O$+1 mol L→$PtL(C_2O_4)$+ $K_2C_2O_4$

Step 3

The crude product may be purified by extracting the oxalatoplatinum(II) complex with sufficient excess of water. Contaminating $K_2Pt(C_2O_4)_2.2H_2O$ which has similar solubility properties to the oxalatoplatinum(II) complex such as oxaliplatin at low temperatures may be removed by transforming it into $Cs_2Pt(C_2O_4)_2$ through addition of $Cs_2C_2O_4$ which upon cooling removes $Pt(C_2O_4)_2^{2-}$. The filtrate of this solution upon vacuum evaporation leaves a solid which can be washed with a small portion of hot water removing the residual amounts of $Pt(C_2O_4)_2^{2-}$ and oxalate salts. The white solid may be washed with cold water to obtain pure oxaliplatin. A further amount of oxalatoplatinum(II) complex may be obtained from the filtrate after removing $Cs_2Pt(C_2O_4)_2$ which precipitates after cooling. The final step consists of the recrystallization of the above white precipitate. A final oxaliplatin product has a chemical purity of >99.5% and optical purity of >99.98%. The overall yield of chemically and optically pure oxaliplatin is 15%.

Thus, the above method of the invention when used for producing oxaliplatin uses only 5 steps with an overall reaction time of 16 hours. It also requires the use of only four different chemicals, namely: $K_2PtCl_6/K_2PtCl_4$, $K_2C_2O_4$, $Cs_2C_2O_4$ and a suitable neutral bidentate ligand.

The method described above may be used to form many other platinum(II) complexes with neutral bidentate ligands, and makes it possible to form platinum(II) complexes with neutral bidentate ligands that contain donor atoms other than N, typically S and Se, for example:

neutral bidentate heterocyclic amines with an S donor atom, such as thioethereal S containing compounds of the general formula:

1-alkyl/aryl-2-alkylthioalkyl/aryl heterocyclic amines, particularly imidazoles or pyridines;
aminoalkylthioalkyl/aryl compounds;
dithioethers for example 2,5-dithiahexane;
diseleno ethers for example 2,5-diseleno hexane; etc.

Ligands containing S and Se donor atoms cannot be used in reactions that make use of silver compounds, because these atoms react by binding very strongly with both platinum and silver ions.

The following 2-methylthioalkyl imidazole and pyridine neutral bidentate ligands:
Ligand (i) 1-methyl-2-methylthioethylimidazole
Ligand (ii) 1-methyl-2-methylthiopropylimidazole
Ligand (iii) 1-butyl-2-methylthiomethylimidazole
Ligand (iv) 1-methyl-2-methylthiomethylimidazole
Ligand (v) 1-butyl-2-methylthioethylimidazole
Ligand (vi) 2-methylthiomethylpyridine
Ligand (vii) 2-methylthioethylpyridine
Ligand (viii) 2-methylthiopropylpyridine (prepared by the methods described in J G H du Preez, T I A Gerber, W Edge, V L V Mtotywa and B J A M van Brecht. Nitrogen Reagents in Metal Ion Separation. XI. The Synthesis and Extraction Behaviour of a New NS imidazole Derivative. Solv. Extr. & Ion Exch. (2001) 19(1), 143-154) (the content of which is incorporated herein by reference) may be used in the below method to prepare the 2-methylthioakyl complexes of imidazole and pyridine (i) to (v) mentioned below.

$K_2Pt(C_2O_4)_2 \cdot 2H_2O$ may be dissolved in distilled water over a 90° C. water bath to which is added dropwise while stirring one molar equivalent of the relevant neutral bidentate ligand dissolved in acetone. The platinum(II) solution so formed may be stirred for 1½ hours at 90° C. and subsequently allowed to cool. The resultant precipitate may be filtered and washed once with cold distilled water and air dried in an oven at 50° C.

Examples of 2-methylthioalkyl complexes of imidazole prepared by the above method are reflected in the structural Formula (I) below where $R_1$ and $R_2$ may be selected from alkyl (e.g. $CH_3$, $C_2H_5$ etc.) and aryl (e.g. phenyl) groups. Typical 2-methylthioakyl complexes of imidazole are complexes (i) to (v) below:

Formula (I)

Complex (i) $R_1=CH_3$ $R_2=C_2H_5$
Complex (ii) $R_1=CH_3$ $R_2=C_3H_7$
Complex (iii) $R_1=C_4H_9$ $R_2=CH_3$
Complex (iv) $R_1=CH_3$ $R_2=CH_3$
Complex (v) $R_1=C_4H_9$ $R_2=C_2H_5$ The chemical names for the complexes (i) to (v) are:
Complex (i) oxalato(1-methyl-2-methylthioethylimidazole)platinum(II)
Complex (ii) oxalato(1-methyl-2-methylthiopropylimidazole)platinum(II)
Complex (iii) oxalato(1-butyl-2-methylthiomethylimidazole)platinum(II)
Complex (iv) oxalato(1-methyl-2-methylthiomethylimidazole)platinum(II)
Complex (v) oxalato(1-butyl-2-methylthioethylimidazole)platinum(II).

Examples of 2-methylthioakyl complexes of pyridine of the invention are reflected in the structural Formula (II) below where $R_2$ may be selected from alkyl (e.g. $CH_3$, $C_2H_5$ etc.) and aryl (e.g. phenyl) groups. Typical 2-methylthioakyl complexes of pyridine are compounds (vi) to (viii) below:

Formula (II)

Complex (vi) $R_2=CH_3$
Complex (vii) $R_2=C_2H_5$
Complex (viii) $R_2=C_3H_7$

The chemical names for the complexes (vi) to (viii) are:
Complex (vi) oxalato(2-methylthiomethylpyridine)platinum(II)
Complex (vii) oxalato(2-methylthioethylpyridine)platinum(II)
Complex (viii) oxalato(2-methylthiopropylpyridine)platinum(II).

2-methylthioakyl complexes of imidazole and pyridine mentioned above have been shown to have anti-cancer properties.

The following ligands:
Ligand (ix) 1-amino-2-thiomethylethane
Ligand (x) 1-amino-2-thioethylethane may be used to prepare an aliphatic aminothioether complex of Pt(II)oxalate, using the method below:

$K_2Pt(C_2O_4)_2 \cdot 2H_2O$ may be dissolved in distilled water over a 90° C. water bath. Dimethylformamide (dmf) may be added to the platinum(II) solution to form a 20:80 water:dmf mixed solvent ratio. One molar equivalent of the relevant ligand may be dissolved in acetone and added dropwise while stirring whereafter the platinum(II) solution so formed may be stirred for 2 hours at 90° C. The reaction may be allowed to cool at room temperature and the resultant precipitate filtered, washed once with cold distilled water and allowed to air dry in an oven at 50° C. to produce a light yellow product (47% yield).

Examples of aliphatic aminothioether complexes of Pt(II) oxalate prepared by the above method are:
Complex (ix) oxalato(1-amino-2-thiomethylethane)platinum(II)
Complex (x) oxalato(1-amino-2-thioethylethane)platinum(II).

The conventional method of preparing oxaliplatin, such as the method described in U.S. Pat. No. 5,420,319, uses 6 steps and has an overall reaction time of 38 hours. The method of the present invention reduces the reaction time and has fewer steps. Thus, the method of the invention is simpler, more efficient and more cost-effective than conventional methods. The method of the invention also eliminates the contamination problems experienced in conventional methods, such as that described in U.S. Pat. No. 5,420,319. No $PtLX_2$ is formed which is generally quite insoluble in water and no silver is used which needs to be removed. The only by-products that need to be eliminated from the method of the invention is excess $K_2C_2O_4$ when synthesizing $K_2Pt(C_2O_4)_2 \cdot 2H_2O$ and unreacted $K_2Pt(C_2O_4)_2 \cdot 2H_2O$ and oxalate salts when producing $PtL(C_2O_4)$ in the case of oxaliplatin. The excess oxalate salts are very soluble in water and can be removed easily by washing with distilled water.

A further advantage of not using a silver compound is that this reaction need not be carried out in darkness and can be used with neutral bidentate ligands that contain donor atoms other than N, such as S and Se which readily react with silver ions. Such ligands cannot be used in the methods that make use of silver compounds, thus preventing the synthesis of their carboxylato analogues. Thus, the method of the invention makes possible, inter alia, the synthesis of bidentate N,N ligand oxalato complexes of platinum(II) and a variety of new oxalatoplatinum(II) complexes containing bidentate ligands with N, S or Se donor atoms. These compounds, according to test results, have application as new anticancer agents which may be used in methods of treating cancer in patients, and in methods of manufacturing medicaments for treating cancer in patients.

The invention will now by described with reference to the following non-limiting examples.

EXAMPLE 1

Production of $K_2Pt(C_2O_4)_2 \cdot 2H_2O$ from $K_2PtCl_4$ 2.075 g (4.6 mmole) $K_2PtCl_4$ and 13.561 g (73.6 mmole) $K_2C_2O_4$ was dissolved in 30 ml distilled water and stirred for 1 hour at approximately 95° C. The reaction vessel was subsequently refrigerated at approximately 5° C. for 2 hours and the precipitate filtered, washed 5 times with 4 ml water, rinsed with 2 ml acetone and air dried in a 50° C. oven. The yield was 98%.

EXAMPLE 2

Production of $K_2Pt(C_2O_4)_2 \cdot 2H_2O$ from $K_2PtCl_6$ with Oxalate as the Reducing Agent 1.425 g (2.9 mmole) $K_2PtCl_6$ and 18.392 g (99.8 mmole) $K_2C_2O_4$ was dissolved in 50 ml distilled water at approximately 95° C. and stirred for 1 hour 15 minutes, subsequently cooled in a refrigerator for 2 hours and filtered. The excess $K_2C_2O_4$ was removed by washing the precipitate 5 times with 3 ml portions of water and rinsed once with 2 ml acetone. It was allowed to air dry in a 50° C. oven. The yield was 86%.

EXAMPLE 3

Production of $K_2Pt(C_2O_4)_2 \cdot 2H_2O$ from $K_2PtCl_6$ with $SO_2$ as the reducing agent 0.326 g (0.67 mmole) $K_2PtCl_6$ was suspended in 6 ml distilled water at approximately 95° C. A saturated $SO_2$ solution was added drop wise till all the $K_2PtCl_6$ dissolved. Excess $K_2C_2O_4$ (1.981 g (10.8 mmole) was added directly to the platinum solution and stirred for a further hour. The mixture was refrigerated for 2 hours and filtered. The precipitate was washed 5 times with 3 ml portions of water, rinsed once with 1 ml acetone and allowed to air dry in a 50° C. oven. The yield was 78%.

EXAMPLE 4

Synthesis of Oxaliplatin $K_2Pt(C_2O_4)_2 \cdot 2H_2O$ (4.50 g, 9.97 mmol) was dissolved in distilled water (815 ml) at 90° C. to provide a platinum oxalate solution. One equivalent of optically pure trans-l-1, 2-diaminocyclohexane (produced by a method as described in Hans-Jörg Schanz, Michael A. Linseis and Declan G. Gilheany, Improved resolution methods for (R,R)- and (S,S)-cyclohexane-1,2-diamine and (R)- and (S)-Binol. Tetrahedron Asymmetry 12 (2003), 2763-2769) (1.06 g, 9.27 mmol) was dissolved in distilled water (74 ml) and the pH adjusted with dilute acetic acid to between 6.6-7.5, to provide an amine solution. The amine solution was added incrementally in eight equal portions every 45 minutes to the platinum oxalate solution over 6 hours where after the solution was cooled to room temperature and the precipitate filtered. The solvent was removed from the filtrate under vacuum. The solid obtained from the filtrate contains oxaliplatin in a crude form.

Figure 3:
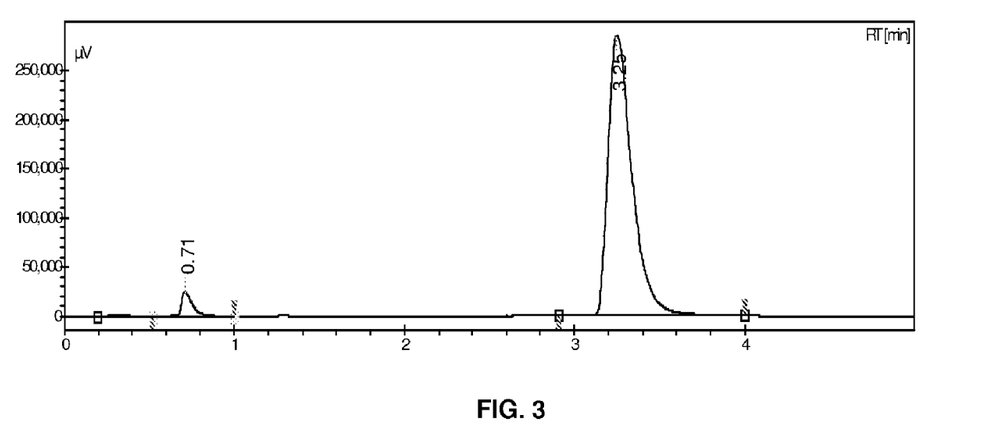
FIG. 3 is a chromatographic analysis of the oxaliplatin product which did not dissolve when suspended in 6 ml water, in Example 4.
Figure 4:
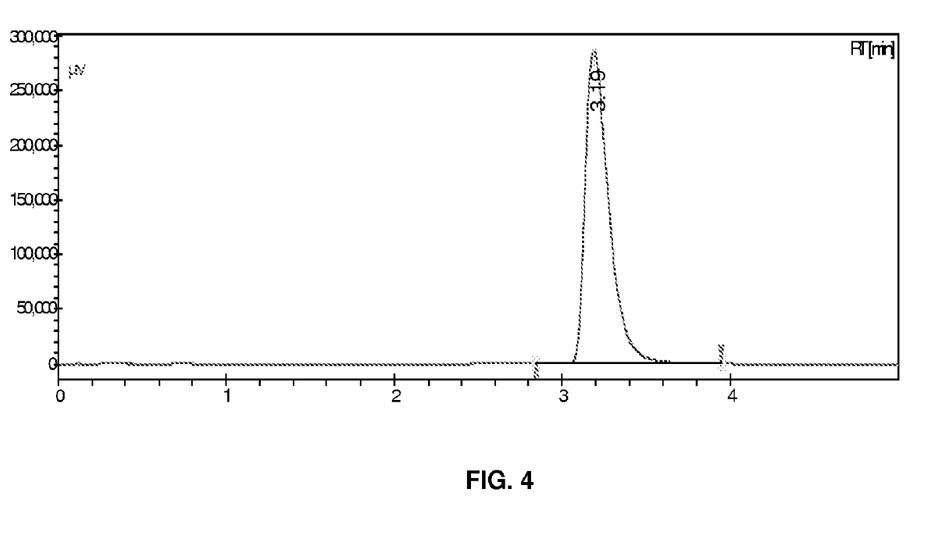
FIG. 4 is a chromatographic analysis of the oxaliplatin product of FIG. 3 which has subsequently been washed with water, in Example 4.

This solid was suspended in distilled water (40 ml) over a water bath at 70° C. for a period of time (10 minutes) where after the remaining solid was removed by filtration. The filtrate was cooled and 0.75 molar equivalents of $Cs_2C_2O_4$ in relation to $K_2Pt(C_2O_4)_2 \cdot 2H_2O$ was added. The solution was stirred for approximately 20 minutes and the precipitate which formed was filtered. The solvent was subsequently vacuum evaporated. The remaining solid was suspended in a small portion of distilled water (6 ml) and heated to 70° C. for a period of time (10 minutes) and filtered to provide a filtrate (A). The solid which did not dissolve contained mostly oxaliplatin with a small portion of oxalate salt (see FIG. 3). This was readily purified by washing the solid with a small portion (3 ml) of distilled water to obtain pure oxaliplatin (see FIG. 4).

The filtrate (A) was cooled to 5° C. and the precipitate filtered. The solvent was vacuum evaporated. The solid which remained contained mainly oxaliplatin and cesium and potassium oxalates. The oxalate salts were readily removed by washing 5 times with small portions of distilled water (3 ml) resulting in a further amount of pure oxaliplatin.

Figure 5:
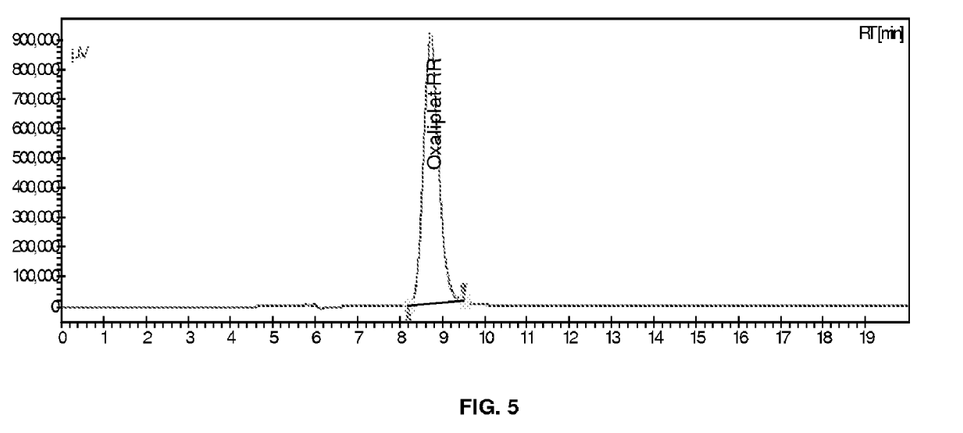
FIG. 5 is a chromatographic analysis of the chemically pure oxaliplatin product of Example 4 as determined on a chiral column indicating its optical purity.

All the oxaliplatin samples produced had a chemical purity>99.5% (see FIG. 4) and optical purity of >99.98% (see FIG. 5).

The overall yield of chemically and optically pure oxaliplatin was 15%.

EXAMPLE 5

Method for Producing Oxaliplatin with $K_2PtCl_4$ as the Starting Material

Both $K_2PtCl_4$ (41.5 g; 92.0 mmole) and 271.17 g (1178.8 mmole) of $K_2C_2O_4$ were simultaneously dissolved in 600 ml water and kept at 95° C. for at least 1 hour, during which time $K_2Pt(C_2O_4)_2 \cdot 2H_2O$ gradually precipitated. The solution was cooled for over 2 hours at 5° C., filtered and washed with 5 80 ml portions of water and finally with acetone. After 45 minutes in an oven at 50° C. pure dry $K_2Pt(C_2O_4)_2 \cdot 2H_2O$ (43.72 g; 89.96 mmole) was obtained. The product was dissolved in 120 ml pure water at 95° C. and trans-l-1,2-diaminocyclohexane (10.28 g; 90.03 mmole) dissolved in 40 ml acetone was added and stirred for 1½ hours at 95° C. It was left to stand at room temperature for over 2 hours, The solvent was removed from the filtrate under vacuum. The solid obtained from the filtrate contained most of the oxaliplatin in a crude form.

This solid was suspended in distilled water (388 ml) over a water bath at 70° C. for a period of time (20 minutes) where after the remaining solid was removed by filtration. The filtrate was cooled and 0.75 molar equivalents of $Cs_2C_2O_4$ in relation to $K_2Pt(C_2O_4)_2 \cdot 2H_2O$ was added. The solution was stirred for approximately 20 minutes and the precipitate which formed was filtered. The solvent was subsequently vacuum evaporated. The remaining solid was suspended in a portion of distilled water (58 ml) and heated at 70° C. for a period of time (20 minutes) and filtered to provide a filtrate (A).

The solid which did not dissolve contained mostly oxaliplatin with a portion of oxalate salt. This was readily purified by washing the solid with a portion (29 ml) of distilled water to obtain pure oxaliplatin.

The filtrate (A) was cooled to 5° C. and the precipitate filtered. The solvent was vacuum evaporated. The solid which remained contained mainly oxaliplatin and cesium and potassium oxalates. The oxalate salts were readily removed by washing 5 times with portions of distilled water (29 ml) resulting in pure oxaliplatin.

All the oxaliplatin samples produced had a chemical purity>99.5% and optical purity of >99.98%. The overall yield of chemically and optically pure oxaliplatin was 15%.

EXAMPLE 6

Method for the Preparation of 2-Methylthioakyl Complexes of Imidazole and Pyridine, in this Case Oxalato(1-Methyl-2-Methylthiopropylimidazole)Platinum(II)

0.68 g of $K_2Pt(C_2O_4)_2 2H_2O$ was dissolved in 40 ml distilled water over a water bath at 90° C. to which was added dropwise while stirring 0.638 g of 1-methyl-2-methylthiopropylimidazole dissolved in 4 ml acetone. The platinum(II) solution was stirred for 1½ h at 90° C. and subsequently allowed to cool overnight. The resultant precipitate was filtered and washed once with a 6 ml portion of cold distilled water and air dried in an oven at 50° C. Light yellow solid (60% yield).

EXAMPLE 7

Method for the Preparation of an Aliphatic Aminothioether Complex of Pt(II) Oxalate, in this Case Oxalato(1-Amino-2-Thiomethylethane)Platinum(II)

$K_2Pt(C_2O_4)_2.2H_2O$ (0.6 mmol; 0.291 g) was dissolved in 8 ml distilled water over a 90° C. water bath. 32 ml dmf was added to the platinum(II) solution to form a 20:80 water:dmf solvent ratio. One molar equivalent (0.6 mmol) of the 1-amino-2-thiomethylethane ligand was dissolved in 3 ml acetone and added dropwise while stirring whereafter the platinum(II) solution was stirred for 2 hours at 90° C. The reaction was allowed to cool overnight at room temperature and the resultant precipitate filtered, washed once with a 3 ml portion of cold distilled water and allowed to air dry in an oven at 50%. Light yellow product 47% yield.

EXAMPLE 8

The purities of the compounds of Examples 6 and 7 were determined by C, H and N analysis, infrared spectroscopy and the ligands by NMR spectroscopy. All the complexes show molecular weight peaks obtained from FAB mass spectral data which correspond with monomolecular complexes except Pt(1-methyl-2-methylthiopropylimidazole)$C_2O_4$ which gave only fractions.

EXAMPLE 9

Anticancer testing on the complex of Example 6 was performed and compared with cisplatin under similar conditions using 5% foetal calf serum as a medium. The percentage inhibition of oxalato(1-methyl-2-methylthiopropylimidazole)platinum(II) on cervical cancer cells was 88.6% and 97.7% at 10 and 100 μM solutions while the corresponding values for cisplatin are 85.4 and 95.3% respectively. A further study in which a medium containing 10 mM glutathione was used the complex performed even better, viz 85% inhibition of colon cancer cells at 100 μM (cisplatin 48%); 72% on breast cancer (cisplatin 10%) at 100 μM solution.

The invention claimed is:

1. A method for the preparation of oxaliplatin, the method comprising reacting a suitable platinum(II) species with trans-1-1,2-diaminocyclohexane, wherein the method does not utilize silver.

2. The method of claim 1, wherein the oxaliplatin preparation has a chemical purity of greater than 99.5%.

3. The method of claim 1, wherein the oxaliplatin preparation has an optical purity of greater than 99.98%.

4. The method of claim 1, wherein the oxaliplatin preparation has a chemical purity of greater than 99.5% and an optical purity of greater than 99.98%.

5. An oxaliplatin product containing no traces of silver, having a chemical purity of greater than 99.5%.

6. An oxaliplatin product containing no traces of silver, having an optical purity of greater than 99.98%.

7. The oxaliplatin product of claim 6, having a chemical purity of greater than 99.5%.

8. A method of treating cancer in a patient, the method comprising administering a therapeutically effective amount of an oxaliplatin product containing no traces of silver to a patient in need thereof.

9. The method of claim 8, wherein the cancer is colon cancer.

10. The method of claim 8, wherein the cancer is cervical cancer.

* * * * *